Figure 1:
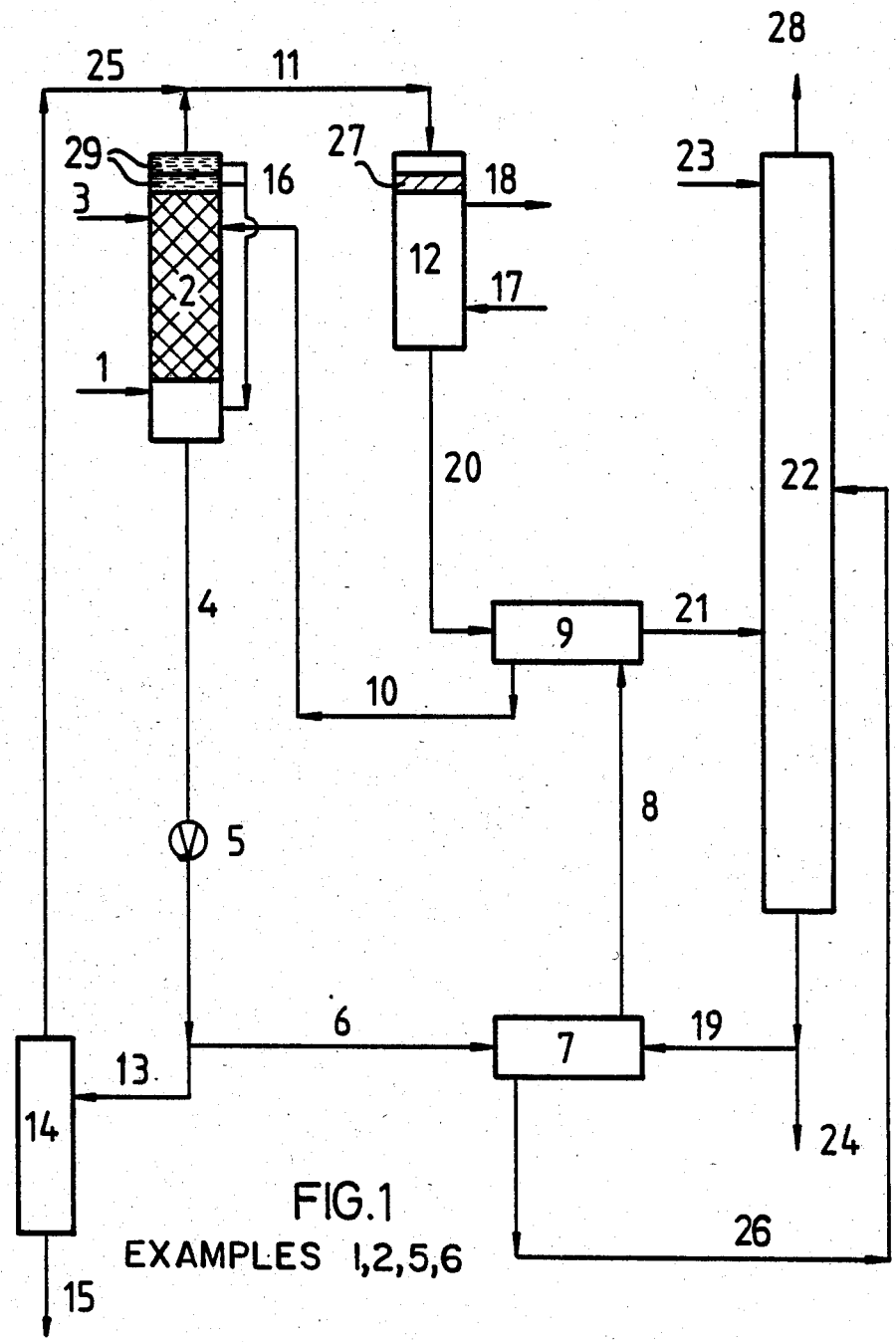

United States Patent [19]

Aicher et al.

[11] Patent Number: 4,584,412
[45] Date of Patent: Apr. 22, 1986

[54] PREPARATION OF FORMALDEHYDE

[75] Inventors: Albrecht Aicher, Frankenthal; Gunter Lehmann, Birkenheide; Norbert Petri, Frankenthal; Walter Pitteroff, Bobenheim; Günter Reuss; Hans Schreiber, both of Ludwigshafen; Robert Sebastian, Deidesheim, all of Fed. Rep. of Germany

[73] Assignee: BASF Aktiengesellschaft, Ludwigshafen, Fed. Rep. of Germany

[21] Appl. No.: 693,864

[22] Filed: Jan. 23, 1985

[30] Foreign Application Priority Data

Jan. 28, 1984 [DE] Fed. Rep. of Germany ....... 3402995

[51] Int. Cl.$^4$ ............................................. C07C 45/29
[52] U.S. Cl. .................................... 568/473; 568/472
[58] Field of Search ........................ 568/471, 472, 473

[56] References Cited

U.S. PATENT DOCUMENTS

| 3,932,522 | 1/1976 | Seither et al. | 568/473 |
| 3,994,977 | 11/1976 | Aicher et al. | 568/473 |
| 4,119,673 | 10/1978 | Aicher et al. | 568/473 |
| 4,343,954 | 8/1982 | Hoene | 568/473 |
| 4,383,123 | 5/1983 | Ferris et al. | 568/473 |
| 4,385,188 | 5/1983 | Ferris et al. | 568/473 |
| 4,454,354 | 6/1984 | Ferris et al. | 568/473 |

FOREIGN PATENT DOCUMENTS

| 0091060 | 10/1983 | European Pat. Off. | 568/473 |
| 0100809 | 2/1984 | European Pat. Off. | 568/473 |
| 2114370 | 3/1972 | Fed. Rep. of Germany | 568/473 |
| 2323758 | 11/1974 | Fed. Rep. of Germany | 568/473 |
| 577573 | 5/1946 | United Kingdom | 568/473 |

OTHER PUBLICATIONS

Ullmanns Encyklopadie der technischen Chemie (4th edition), 11, p. 692.
BIOS, Final Report, No. 978, Item No. 22, p. 43.
Ullmanns Encyklopadie der technischen Chemie (3rd edition), 12, pp. 398-420, 670.
BIOS, Final Report No. 1331.
FIAT Final Report No. 999.
W. L. Badger and J. T. Banchero (McGraw-Hill Book Company Inc. 1955), p. 437.

Primary Examiner—Werren B. Lone
Attorney, Agent, or Firm—John H. Shurtleff

[57] ABSTRACT

Formaldehyde is prepared by (a) passing a mixture of methanol and water with a concentration of between 50 and 90% by weight, based on the total weight of the two substances, of methanol into a packed column which possesses a packing having a total layer thickness of not less than 50 cm and a total surface area of not less than 0.5 cm$^2$ per cm$^3$ of packing, a liquid circulation of from 15 to 90 g/min per g/min of methanol fed to the column, and a concentration of from 10 to 45% by weight of methanol in the recycle liquid, the temperature at the point of entry of the recycle liquid in the column being from 50° to 86° C. and the bottom temperature being 10°-25° C. lower than this, i.e. from 40° to 70° C., (b) separating off methanol and water from the column by stripping with air, an inert gas and/or exit gas, the throughput being from 0.5 to 3 tonnes of methanol and water per hour per m$^2$ of column cross-section, (c) converting the gaseous mixture of methanol, water, air, inert gas and/or exit gas at a space velocity of from 0.5 to 3 tonnes of methanol per m$^2$ of catalyst bed cross-section per hour, in the presence of a silver catalyst at from 550° to 750° C. and (d) finally, cooling and absorbing the hot reaction gases, and using the resulting heat of absorption and, if desired, the heat of reaction and/or the heat of condensation partially or completely for heating the recycle liquid, methanol containing impurities being used if desired and, after the stages (a) and (b) and before the stages (c) and (d), the measures of a stage (e) being carried out, wherein the gaseous mixture formed is passed through two layers of wire filter having a wire diameter of from 0.1 to 0.5 mm and a free layer volume of from 90 to 99.5 vol. %, based on the total volume of one wire layer, at a flow rate of from 7 to 13 m/sec in the first layer, and from 1 to 4 m/sec in the second layer.

The formaldehyde obtainable by the process of the invention is a disinfectant, tanning agent, reducing agent and a useful starting material for the preparation of synthetic resins, adhesives and plastics.

18 Claims, 2 Drawing Figures

EXAMPLES 1,2,5,6

EXAMPLES 3 & 4

PREPARATION OF FORMALDEHYDE

The present invention relates to a process for the preparation of formaldehyde by (a) passing a mixture of methanol and water with a concentration of between 50 and 90% by weight, based on the total weight of the two substances, of methanol into a packed column which possesses a packing having a total layer thickness of not less than 50 cm and a total surface area of not less than 0.5 cm$^2$ per cm$^3$ of packing, a liquid circulation of from 15 to 90 g/min per g/min of methanol fed to the column, and a concentration of from 10 to 45% by weight of methanol in the recycle liquid, the temperature at the point of entry of the recycle liquid into the column being from 50° to 86° C. and the bottom temperature being 10°–25° C. lower than this, i.e. from 40° to 70° C., (b) separating off methanol and water from the column by stripping with air, an inert gas and/or exit gas, the throughput being from 0.5 to 3 tonnes of methanol and water per hour per m$^2$ of column cross-section, (c) converting the gaseous mixture of methanol, water, air, inert gas and/or exit gas at a space velocity of from 0.5 to 3 tonnes of methanol per m$^2$ of catalyst bed cross-section per hour, in the presence of a silver catalyst at from 550° to 750° C. and (d) finally, cooling and absorbing the hot reaction gases, and using the resulting heat of absorption and, if desired, the heat of reaction and/or the heat of condensation partially or completely for heating the recycle liquid, methanol containing impurities being used if desired and, after the stages (a) and (b) and before the stages (c) and (d), the measures of a stage (e) being carried out, wherein the gaseous mixture formed is passed through two layers of wire filter having a wire diameter of from 0.1 to 0.5 mm and a free layer volume of from 90 to 99.5 vol. %, based on the total volume of one wire layer, at a flow rate of from 7 to 13 m/sec in the first layer, and from 1 to 4 m/sec in the second layer.

Ullmann, Encyklopädie der technischen Chemie (4th edition), 11, page 692, discloses that a 60% strength by weight aqueous methanol solution can be vaporized, mixed with air, and converted in the presence of a silver catalyst. BIOS, Final Report, No. 978, Item No. 22, page 43, discloses that the air can also be fed through the bottom of the evaporator, which is kept at 87° C., and the starting mixture for the reaction prepared in this manner. In the evaporator, which is heated externally by steam, 55% strength aqueous methanol solutions are vaporized. These processes are carried out using pure methanol.

Depending on the method of preparation (Ullmanns Encyklopadie der technischen Chemie (3rd edition), volume 12, page 398 et seq.), crude methanol can vary in its composition, and generally contains from 95 to 70% by weight of methanol, from 1 to 29.9% by weight of water and from 0.1 to 6% by weight of impurities. Depending on the preparation and storage, possible impurities are, for example, alkali metal salts, such as sodium formate, sodium bicarbonate, sodium carbonate, sodium acetate, sodium sulfide, potassium methylate, sodium methylate, potassium hydroxide or sodium hydroxide, formic acid, aldehydes, such as acrolein, glyoxal, butyraldehyde, propionaldehyde or acetaldehyde ketones, such as acetone or butan-2-one, glycol, diglycol and triglycol, higher alkanols, such as N-butanol, isobutanol, isopropanol, n-propanol, n-pentanol, isohexanol, isoheptanol or n-hexanol, ethers, such as glycol methyl ether, diglycol methyl ether or dimethyl ether, aliphatic, cycloaliphatic and aromatic hydrocarbons, such as benzene, toluene, xylene, decane, undecane, dodecane, cyclohexane or ethylbenzene, organic and inorganic compounds, e.g. formates, chlorides or sulfides of metals such as iron, chromium, copper, aluminum, zinc and magnesium, sulfur compounds, such as dimethyl sulfide, esters, e.g. dimethyl terephthalate, amines, such as monomethylamine, dimethylamine or trimethylamine, and ammonia. As a rule, alkaline impurities in particular are present, since the acid present in the methanol is neutralized with alkali in virtually every method of synthesis.

When the crude methanol is vaporized by the conventional methods, not only vapor-phase impurities but also liquid and solid impurities enter the vapor-phase starting mixture of the formaldehyde synthesis, for example in the form of finely divided droplets or solids, or liquid mists. During the reaction of the methanol, they promote side reactions or attack the catalyst, for example by destroying the active surface of the silver or by depositing solids or resin-like substances on the catalyst, and reduce its life and hence the yield of end product and the cost-efficiency of the process. Moreover, by blocking the feedlines or causing corrosion on the metal surfaces, deposits can cause substantial disruption in the operation of a plant. The catalyst, which consists of granules composed of silver particles, gradually loses its gas permeability as a result of the deposits. The pressure loss at the catalyst layer increases and results in greater energy consumption for the air compression. The required amount of air can no longer be fed through with the blowers generally employed, and the conversion of the plant falls; this forces a premature shutdown of the plant in order to replace the catalyst. This is another reason for loss of yield. Moreover, a shorter catalyst life means extra costs for changing and regenerating the catalyst.

Another cause of catalyst poisoning is the action of harmful foreign substances which are present in the air used for the oxidation. Such atmospheric impurities are present to a particularly great extent in the region of industrial conurbations and contain, for example, the following catalyst-poisoning components: hydrogen sulfide, sulfur dioxide, hydrogen chloride, hydrogen fluoride, halogens, volatile halogen compounds, such as carbon tetrachloride, ammonia, amines, such as monomethylamine, dimethylamine and trimethylamine, arsenic and antimony compounds, such as arsenic trioxide and antimony trioxide, acetylene, phosphorus compounds such as hydrogen phosphide, carbon black, iron oxide dust, hydrogen cyanide, carbon monoxide, foreign substances, such as mercaptans, indole or skatole, which are formed from the anaerobic decomposition of protein-containing wastes, nitrogen oxides, lead compounds such as tetraethyland tetramethyl-lead, and organic compounds, such as 3,4-benzopyrene, fluoranthene, pyrene or phenanthrene, which enter the air through automobile exhaust gases, and their oxidation products, such as acrolein. In general, the amount of foreign substances in the air is from 0.01 to 10 ppm.

The water used in the formaldehyde synthesis is condensation water, but chlorine-free process water, which advantageously has been softened, is also employed. Suitable process water in this context is groundwater, spring water, surface water such as river water, tap water, boiler feed water and sometimes also sea water. Depending on origin and processing, the water used can contain a large number of substances as impurities, for example metal salts, such as manganese sulfate and iron chloride, alkaline earth metal compounds in the form of water hardness, ammonium salts, alkali metal salts, metals such as zinc or aluminum or copper, for example from raw materials, nitrates, silicates, nitrites, fluorides, phosphates and organic decomposition products, such as phenols.

When such mixtures of methanol and water are vaporized, considerable difficulties frequently occur: the rate of vaporization decreases, the bottom of the evaporator retains liquid, and fairly large amounts of foam occur on the surface of the methanol solution being vaporized, the foam possessing relatively large individual bubbles and generally having a fairly firm consistency. At the same time, the pressure in the evaporator can increase, and the liquid, mixing with the air, can form an increasing amount of a dense foam layer over a period of time. In some cases, the foam is entrained, reaches the catalyst and interferes with or prevents the conversion of the methanol. Particularly in large-scale industrial operation, where in general from 1,000 to 20,000 kg/hour of methanol solution are vaporized from 60–95% strength by weight methanol solutions, the pressure can increase from the usual value of 1.2 bar to 1.5–1.8 bar after from 1 to 16, frequently from 1 to 3 hours when a two-tray evaporator column is used. At the same time, the amount of solution vaporized per hour decreases to 70–80% of its initial value. All these difficulties generally result in substantial operating problems or failures. In any case, the feed and the heat supply have to be interrupted.

In the conventional processes, operating difficulties also arise during start-up of the evaporation units, particularly after operating problems or shutdown of the units. In such cases, air becomes available very rapidly since the blowers reach full capacity rapidly. However, valuable time is consumed in heating up the evaporator. Hence, relatively large amounts of liquid are required on each tray as a heat store, so that the heat is available for vaporization, which has to take place quickly. However, bubble tray columns and packed columns empty rapidly. Sieve tray columns of conventional design are also of little use in this case; they are sensitive to fluctuations in throughput, and likewise require a fairly long time to be heated up. Moreover, they tend to cause difficulties when the vapor passes through the sieve holes, since the liquid collected on the trays is entrained, in the form of drops, by the vapor, or, frequently, the liquid blocks the holes and weeping takes place.

Valve tray columns are expensive and offer high resistance when the throughput is high. Moreover, the valves do not close completely tightly after prolonged operation, so that these columns too empty rapidly. Furthermore, in the stated preparation processes, the throughput is particularly high since the vapor mixture and air serve as a starting mixture for the formaldehyde preparation. When a plant is put into operation, the gas mixture consisting of air and vapor bubbles only very sluggishly through the liquid in the vaporization space, the reasons for this being as stated above. Exchange between the vapor and the liquid takes place to an insufficient extent if at all, since little intermixing occurs. The result is a sharp increase in the concentration of methanol in the bottom of the evaporator, and hence pollution of the wastewater, which gives rise to environmental problems and reduces the cost-efficiency of the process. Finally, it must be ensured that at any time, even when the throughput is low, a sufficient amount of methanol is vaporized when the air is passed through; otherwise, explosive air-rich mixtures are formed. Hence, for the stated reasons, after every shutdown of the plant special operations are required for start-up.

German Laid-Open Application DOS No. 2,323,758 describes various prior industrial processes and a process which is more advantageous with regard to the above difficulties. The procedure is carried out as follows: in a tray column containing a plurality of perforated bubble trays, each of which possesses an upper sieve tray, descending toward the outside and having a hole diameter of 2 to 15 mm, and a lower plate-shaped tray ascending towards the outside, the sieve tray making an angle of from 2° to 10° with the horizontal and the lower tray making an angle from 4° to 20° with the horizontal, methanol and water are mixed with air and vaporized, the liquid substance being fed in at the top and the air at the bottom of the column, and the resulting vapor-phase starting mixture is dehydrogenated under oxidizing conditions. However, this process too has disadvantages; the sieve trays are complicated to operate and expensive to manufacture.

According to German Laid-Open Application DOS No. 2,114,370, the apparatuses for vaporizing methanol are generally equipped with droplet separators (BIOS Final Report No. 1331; FIAT Final Report No. 999), e.g. Raschig ring packings or wire net packings. Such packings have a certain effect until they contain sufficient liquid. Thereafter, some of the liquid passes through and is atomized to droplets or mists behind the packing. Hence, these measures too cannot prevent substantial formation of deposits on the catalyst. German Laid-Open Application DOS No. 2,114,370 therefore points out that, for the stated reasons, crude methanol cannot be used for the preparation of formaldehyde on a large industrial scale. Further conventional industrial measures for the use of crude methanol, e.g. distillation, treatment of the methanol with alkalis and/or oxidizing agents, or the preparation of formaldehyde by a low pressure process, are described, and the disadvantages of the corresponding processes are stated.

German Laid-Open Application DOS No. 2,114,370 recommends a process which is more advantageous compared with this prior art and uses crude methanol as a starting material. In this process, the crude methanol in vapor form is fed against baffles before entering the catalyst zone, and the impurities obtained on the baffles in solid or liquid form are separated off. The vapor/gas stream fed against the baffles advantageously has a velocity of from 7 to 22 m/sec. In all of the Examples, a flow rate of 9.2 m/sec is used and homogeneous metal baffles are employed. However, the purifying effect of the baffles, the yield of formaldehyde and the life of the catalyst are unsatisfactory.

We have found that formaldehyde is advantageously obtained by oxidative dehydrogenation of methanol as a mixture with water, in the presence of a silver catalyst at elevated temperatures, and subsequent cooling and absorption of the hot reaction gases, if (a) a mixture of methanol and water with a concentration of from 50 to 90% by weight, based on the total weight of the two substances, of methanol is passed into a packed column which possesses a packing, having a total layer thickness of not less than 50 cm and a total surface area of not less than 0.5 $cm^2$ per $cm^3$ of packing, a liquid circulation of from 15 to 90 g/min per g/min of methanol fed to the column, and a concentration of from 10 to 45% by weight of methanol in the recycle liquid, the temperature at the point of entry of the recycle liquid into the column being from 50° to 86° C. and the bottom temperature being 1°–25° C. lower than this entry temperature, i.e. from 40° to 70° C., (b) methanol and water are separated off from the packed column with air, an inert gas and/or exit gas by stripping, the throughput being from 0.5 to 3 tonnes of methanol and water per hour per m$^2$ of column cross-section, (c) the resulting gaseous mixture of methanol, water, air, inert gas and/or exit gas is converted, at a space velocity of from 0.5 to 3 tonnes of methanol per m$^2$ of catalyst bed cross-section per hour, in the presence of a silver catalyst and at from 550° to 750° C., and (d) finally, the hot reaction gases are cooled and absorbed, the resulting heat of absorption and, if desired, the heat of reaction and/or the heat of condensation being partly or completely used for heating the recycle liquid.

We have furthermore found that the process according to the invention can advantageously be carried out if methanol containing impurities is used and the measures of stages (a) and (b), then the measures of stage (e), wherein the resulting gaseous mixture of methanol, water, air, inert gas and/or exit gas is passed through two layers of wire filter having a wire diameter of from 0.1 to 0.5 mm and a free layer volume of from 90 to 99.5 vol. %, based on the total volume of one wire layer, at a flow rate of from 7 to 13 m/sec in the first layer, and of from 1 to 4 m/sec in the second layer, and finally, using the gaseous mixture, the measures of stages (c) and (d) are carried out.

The present invention is based on the observation that trouble-free continuous operation using methanol, in particular crude methanol, as a starting material cannot be achieved by one measure alone, e.g. a special vaporization, conversion or purification method for the starting materials or maintaining a particular space velocity, but requires the combination of the associated features according to the invention. Compared with the conventional processes which use pure methanol, the process according to the invention gives formaldehyde by a simpler and more economical route and in good yield and purity. With regard to the syntheses using crude methanol as a starting material, the novel process gives formaldehyde in better yield, space-time yield and purity. Liquid mists and finely divided solids or droplets of the corresponding solutions are substantially separated off. The abovementioned difficulties and operating problems are avoided, and the life of the catalyst is correspondingly increased. Rapid poisoning of the catalyst by the reaction air, crude methanol or water of reaction, and corresponding concentration of foreign substances in the solution of the end product, are avoided. The first start-up of a plant, or the subsequent start-up, is simpler, faster and more trouble-free, and the shutdown time of the plants as a result of catalyst poisoning or problems with the evaporator is reduced. According to the invention, methanol and water are separated off from the packed column by stripping, and correspondingly by evaporation and not by vaporization, and are fed to the reaction as a gaseous mixture, if appropriate via the two wire filter layers, so that the energy additionally required for vaporization is saved. Furthermore, corresponding heating means for the vaporization, for example external heating with additional steam or passage of additional steam into the bottom of the evaporator, are not required. On the other hand, it is sufficient to heat the recycle liquid by heat exchange with the hot reaction gases, condensates and/or absorption solutions of the formaldehyde in order to reach the temperatures according to the invention for the stripping process (stripping temperature). This is advantageous in that it simultaneously ensures economical use of the heat of reaction, heat of absorption and/or heat of condensation.

In view of the prior art, all these advantageous results are surprising. Particularly in large-scale industrial operation, it is in general not analytically pure methanol which is used but pure methanols containing less than 0.15% by weight of impurities and, if appropriate, crude methanols having the abovementioned, higher concentrations of impurities. In view of the prior art, it was to be assumed that, in the stripping operation, substantially larger amounts of impurities would be entrained and would have an adverse effect on the catalyst, since the recycle liquid becomes enriched with the impurities.

It was also surprising that the heat of reaction, the heat of absorption and the heat of condensation, which are used for heating the absorption solution and hitherto had to be removed by means of special cooling units in the absorption stage are reused economically, according to the invention, in the same plant and are sufficient for the formation of the vapor-phase methanol/water mixture, since the amount of heat which can be transferred by heat exchange with the absorption solutions, which are generally at from 55° to 85° C. is insufficient to achieve appropriate vaporization of the water/methanol mixture. It is therefore surprising that heat exchange with the absorption solution alone is also sufficient, and furthermore the gas/vapor phase of methanol and water is formed by stripping and corresponding evaporation alone; nevertheless, in the novel process, advantageous results are obtained, and in particular excess heat energy (heat of reaction and heat of condensation) is provided for other uses. Furthermore in view of the conventional processes which always employ a higher temperature (corresponding to the boiling point of water) at the bottom and relatively low temperatures at the top of the column, it was not to be expected that the lower temperatures according to the invention and moreover the temperature gradient from the entrance of the column (higher temperature) to the bottom (lower temperature) would give advantageous results. In view of the conventional evaporator columns, the advantageous use of a packed column was also surprising.

In evaporator columns, it is frequently necessary to separate off some of the bottom liquid in order to reduce the concentration of impurities and hence the above difficulties during the vaporization. In the novel process, not more than 100% by weight, based on the total amount of bottom liquid separated off per hour in a vaporization process, must be separated off per hour. This feature of the novel process is surprising, particularly in view of German Laid-Open Application DOS No. 2,323,758, since, in view of the concentration of impurities in the recycle liquid entering the upper part of the column, which concentration is higher compared with the crude methanol feed, a larger amount of entrained impurities in the gas mixture and hence poorer yields and a shorter catalyst life would have to be expected.

Starting materials used for the process are air, water, and methanol prepared by a high pressure or low pressure method. If water-containing methanol, in particular crude methanol, is used, the addition of further water can be partly or completely dispensed with. Advantageously, instead of separate feeds, a mixture of crude methanol with water is fed into the packed column. The concentration of methanol in the aqueous mixture can advantageously vary from 50 to 90, preferably from 60 to 85%, by weight; accordingly, in the case of separate feeds, it is advantageous to use between 0.11 and 1, preferably from 0.18 to 0.67, g of water per g of methanol. In general, the impure methanol used is a crude methanol containing from 0.15 to 6, advantageously from 0.15 to 5, in particular from 0.15 to 4%, by weight of impurities. Methanol, water and air are reacted as a vapor-phase/gaseous starting mixture advantageously in a ratio of from 0.25 to 0.6, preferably from 0.35 to 0.5, mole of oxygen, in the form of air, per mole of methanol, and from 0.1 to 2, preferably from 0.2 to 1.2, moles of oxygen, in the form of air, per mole of total water present in the starting mixture. Advantageously, the feed rate of liquid and of air, inert gas and/or exit gas to the packed column is appropriately controlled so that the composition of the mixture entering the reaction space conforms to these molar ratios. The throughputs employed through the packed column are from 0.5 to 3 tonnes of freshly fed in water and methanol and, advantageously, from 1.2 to 4.5 tonnes of air or from 0.4 to 2.5 tonnes of inert gas or from 0.4 to 2.5 tonnes of exit gas or from 1.6 to 7.0 tonnes of a mixture of 2 components or of all three components air, inert gas and exit gas, the throughputs being per hour per $m^2$ of column cross-section.

For stripping in the packed column, it is possible to use three components (stripping gas) i.e. air, inert gas and exit gas, either each component alone or a mixture of 2 components or of all three components as the stripping gas. A preferred stripping gas is (b1) air or (b2) a mixture of air and exit gas. When mixtures are used as the stripping gas, it is possible to introduce each of the abovementioned components separately from one another or in the form of a mixture into the packed column. In the case of the three components, it is possible to feed in some of the components, advantageously air, for stripping and to introduce the remainder, after it has passed through the column and, where relevant, the wire layers, into the vapor-phase/gaseous starting mixture, this advantageously being done upstream of the reactor inlet. In a preferred embodiment, a mixture of air and exit gas is fed through the column as a stripping gas, and a further part of air, advantageously from 3 to 20% by weight, based on the total amount of air used, is added to the vapor-phase/gaseous starting mixture (air, exit gas, methanol and water). Expediently the amounts chosen are from 20 to 100, advantageously from 40 to 80, % by weight of inert gas, preferably nitrogen, and/or from 20 to 100, advantageously from 40 to 80%, by weight of exit gas, based on the total weight of air. In an advantageous embodiment, some of the exit gas from the oxidation according to the invention is allowed to escape, and the remainder is returned to the reaction cycle. The amount of exit gas expediently mixed with air and recycled to the reaction in this form is advantageously from 20 to 110, in particular from 44 to 88%, by weight, based on the amount of exit gas leaving the plant. The exit gas essentially contains nitrogen, hydrogen, carbon dioxide, carbon monoxide, water, methanol, argon and, as a rule, from 0.1 to 0.5 g of formaldehyde per $m^3$ of exit gas. When relatively large amounts are converted, the exit gas used may also be the exit gas removed from another formaldehyde preparation by oxidative dehydrogenation of methanol, preferably in the presence of silver catalysts or of metal oxides, for example oxides of iron and of molybdenum.

The packed column advantageously has a length from 2 to 15, in particular from 3 to 10, m and a diameter from 0.5 to 5, in particular from 1 to 3.5, m and contains a packing in which, advantageously, the individual packing elements have a diameter of from 15 to 150, in particular from 25 to 80, mm. The total thickness (height) of the packing layer is not less than 50, advantageously from 100 to 1,000, in particular from 300 to 800, cm. The total surface area of the packing is not less than 0.5, advantageously from 0.5 to 2.2, preferably from 0.9 to 1.6, $cm^2$ per $cm^3$ of the packing layer. Examples of packings which can be used are Raschig rings, Intos rings, Prym rings, Pall rings, Berl saddles, Intalox saddles, Torus saddles, Interpack packings, Stedman packings, oblique pieces of film, wire mesh rings, Haltmeier rolls, twinned packings, Wilson spirals or Brunswick spirals.

As a rule, methanol and water are introduced at the bottom of the column, separately, or, in general, as a mixture, and air, inert gas and/or exit gas, if appropriate as a mixture, are introduced at the bottom of the column; in a preferred embodiment, air or one of the abovementioned air mixtures is passed through the bottom of the column. The columns have a liquid circulation which, as a rule, starts from the bottom of the column and ends at the top of the column, advantageously from 30 to 200 cm below the top of the column. The recycle liquid advantageously has a throughput of from 3,000 to 6,000, in particular from 3,500 to 5,500, g per $cm^2$ of column cross-section per hour, and is generally fed via heat exchangers, wherein they serve as cooling liquid for the hot reaction gases, condensates and absorption solutions. If required, some of the heat present in the recycle liquid can be exchanged with the hot reaction gases and/or absorption solutions from another formaldehyde synthesis or formaldehyde secondary reaction, or in the heat exchangers of another synthesis. In any case, some or all, advantageously from 40 to 70, preferably from 50 to 60%, (based on the total heat fed to the liquid circulation), of the heat of absorption obtained in the absorption of formaldehyde from the hot reaction gases and/or condensates, advantageously in water or aqueous urea solution, must be used for heating the liquid circulation. The aqueous urea solution advantageously contains from 50 to 70, preferably from 65 to 70%, by weight of urea.

Advantageously, the recycle liquid is an aqueous methanol mixture which contains from 10 to 45, in particular from 15 to 40, % by weight of methanol (calculated as 100% pure methanol) and from 0.1 to 15, in particular from 1 to 10, % by weight of impurities. The circulation brings liquid to the column in a ratio of from 15 to 90, in particular from 20 to 70, g/minute per g/minute of fresh methanol fed to the column, and its temperature at the entrance to the column is from 50° to 86° C., in particular from 60° to 80° C., and its temperature at the bottom of the column is from 40° to 70° C., in particular from 45° to 60° C. The bottom temperature is from 10° to 25° C., advantageously from 15° to 20° C., lower than the temperature of the recycle liquid at its point of entry. If necessary, in order to remove large amounts of impurities, a small part of the recycle liquid, advantageously from 0.01 to 0.1% by weight of the recycle liquid stream, can be separated off and discarded, and, if desired, the methanol and water present in this part can be isolated via an evaporator or stripper and recycled to the reaction. To vaporize these amounts, the heat of reaction and heat of condensation liberated during cooling of the hot reaction gases can likewise advantageously be used, for example in the form of excess steam generated by heat exchange.

Air, inert gas and/or exit gas serve as an entraining agent (stripping agent) for the methanol/water mixture fed to the column, for the recycle liquid and, where the gases are passed through the bottom, for the bottom liquid; the composition of the bottom liquid corresponds to that of the recycle liquid when it enters the column. In conformity with a definition in "Introduction to Chemical Engineering" by W. L. Badger and J. T. Banchero (McGraw-Hill Book Company Inc. 1955), page 437 (last paragraph), the procedure described is referred to here as stripping. The gas feed is chosen so that an equilibrium is established between the abovementioned throughputs of water/methanol mixture, recycle liquid and gas and the above ratios of the components air, inert gas, exit gas, methanol and water in the conversion. The major part of the methanol and water separated off in the column by stripping is gaseous and contains in general less than 0.1% of weight of liquid methanol/water mixture and in general less than 0.01% by weight of liquid and solid impurities.

The amount of methanol in the gas phase is in general from 50 to 90, in particular from 60 to 85%, by weight, calculated as 100% pure methanol and based on the total amount of water and methanol in this phase. Where crude methanol is used, the gaseous mixture, after being subjected to stages (a) and (b) is advantageously subjected to stage (e), in which it is passed through 2 layers of wire filter. In this context, wire filter comprises wire structures which can have any desired structure, either regular or irregular, for example in the form of woven materials, meshes, nets, coils or spirals, and are combined to form two separate layers, for example in two packings. The wire in the two layers has a diameter (thickness) of from 0.1 to 0.5, advantageously from 0.1 to 0.3, mm, and each of the two layers has a free volume of from 90 to 99.5, in particular from 95 to 99.1, vol. %, based on the total volume of the layer, the free volume of the layer being defined in this case as the total volume of the layer which is not occupied by the volume of the wire. The gas stream flows through the first layer at a rate of from 7 to 13, in particular from 9 to 11, m/sec and advantageously with a throughput of from 12 to 60, in particular from 20 to 51, g of methanol per minute per $cm^2$ of layer cross-section, and through the second layer at a rate from 1 to 4, in particular from 1.5 to 3.5, m/sec and advantageously with a throughput of from 1 to 20, in particular from 1.5 to 18, g of methanol per minute per $cm^2$ of layer cross-section. Each of the two layers is advantageously from 10 to 40, in particular from 20 to 30, cm thick.

The gaseous mixture is fed to the reactor containing the silver catalyst in stage (c), this step advantageously being carried out after stage (b), and stage (e) being omitted, in the case of pure methanol, or preferably after passage through the two wire layers in the case of crude methanol. The amount of impurities present in the mixture is then less than 2, in general from 0.01 to 1%, by weight, based on the total amount of impurities in the crude methanol, and from 0.00014 to 0.014% by weight, based on the gaseous methanol (calculated as 100%).

Suitable catalysts for the process according to the invention are the silver catalysts generally used for the preparation of formaldehyde, for example those described in German Published Application DAS No. 1,231,229, German Pat. No. 2,322,757, and Ullmanns Encyklopädie der technischen Chemie (3rd edition), volume 7, page 656 et seq., and in the publications stated in connection with the prior art. Preferably, two-layer and multi-layer silver catalysts are used. Regarding the preparation of the catalyst and the procedure of the corresponding conversion with these catalysts, reference may be made to the stated publications. In a preferred embodiment, the conversion is carried out using a catalyst which has a total layer thickness of from 15 to 35 mm and 3 or more layers of silver crystals, some of the layers containing from 72.5 to 89% by weight of the catalyst and having a particle size of from 1 to 2.5 mm, some of the layers containing from 2.5 to 7.5% by weight of the catalyst and having a particle size of from 0.75 to 1 mm, and the remaining layers containing from 8.5 to 20% by weight of the catalyst and having a particle size of from 0.2 to 0.75 mm. Preferred catalyst are those described in German Pat. No. 2,322,757.

The space velocity during the oxidation is from 0.5 to 3, in particular from 1 to 2.50, g of methanol (calculated as 100% pure) per $m^2$ of catalyst bed cross-section per hour.

The oxidation is in general carried out in a conventional manner by, for example, passing the gas mixture consisting of methanol vapor, air, steam and, if required, inert gas and/or exit gas in the above amounts, at from 550° to 750° C., in particular from 600° to 700° C., through the silver catalyst. The reaction is generally carried out under a pressure of between 0.5 and 2, preferably between 0.8 and 1.8, bar, by a continuous procedure. In this case, it is advantageous if, in stage (d), the reaction gases leaving the catalyst zone are cooled within a short time, for example in less than 1/10 second, to, for example, 150°–350° C. The cooled gas mixture is then advantageously (d1) fed to a condenser for further cooling and then to the absorption stage, or (d2) fed directly, without condensation, to an absorption tower, in which the formaldehyde is generally washed out of the gas mixture with water or an aqueous urea solution, advantageously by a countercurrent method.

The abovementioned heat exchanger for heat exchange between the reaction gas and/or condensate and the recycle liquid is advantageously located between the reactor and the absorption tower, while the abovementioned heat exchanger for heat exchange between the recycle liquid and the hot absorption solution is located in the circulation of the absorption unit. Advantageously, from 10 to 100, in particular from 40 to 100%, of the amount of heat used to adjust the temperature of the recycle liquid originates from the heat exchange with the absorption solution, from 0 to 90, in particular from 0 to 60%, of this heat originates from the condensation, and from 0 to 50, in particular from 0 to 30%, of this heat originates from cooling of the reaction gases.

The formaldehyde which can be prepared by the process of the invention is a disinfectant, a tanning agent, a reducing agent and a useful starting material for the preparation of synthetic resins, adhesives and plastics. Regarding its use, reference may be made to volume 12 of Ullmann (3rd edition), page 670, as stated above.

The invention is further illustrated by the following examples taken with the drawing in which:

FIG. I is a flow sheet of the process carried out in Example 1, 2, 5, and 6; and FIG. II is a flow sheet of the process carried out in Example 3, and 4.

EXAMPLE 1

(Figure 1)

22,030 kg/hour of air were fed through line (1) to the packed column (2) below the surface of the bottom product of the column. Using a countercurrent procedure, 17,310 kg/hour of a crude methanol/water mixture (1% by weight of impurities, 69.6% by weight of methanol and 29.4% by weight of water) fed via line (3) and 310,000 kg/hour of bottom product (recycle liquid) of the packed column were fed via line (4), pump (5), line (6), heat exchanger (7), line (8), condenser (9) and line (10). The packed column had a length of 12.8 m and a diameter of 300 cm and contained 42 m³ of Pall rings as packing (length 3.5 cm; diameter 3.5 cm). The bottom product (recycle liquid) contained 10% by weight of impurities, 28% by weight of methanol and 62% by weight of water. In heat exchanger (7), the recycle liquid was heated to 68° C., heating being carried out indirectly with absorption liquid via line 19 by a countercurrent procedure. In condenser (9), the recycle liquid was heated indirectly by heat exchange with hot reaction gases (via line (20)) to 79° C. The temperature at the point of entry of the recycle liquid into the column (2) was 78° C., and the bottom temperature of the column (2) was 62° C. 1,730 kg/hour of recycle liquid were taken off via line (13) and were vaporized in evaporator (14), together with 3,343 kg/hour of water. 572 kg/hour of bottom product from the evaporator (172 kg of impurities and 400 kg of water) were taken off via the bottom outlet (15). The amount vaporized per hour (485 kg of methanol, 4,015.99 kg of water and 0.01 kg of impurities) was fed from evaporator (14) via line (25) to line (11). The throughput through the packed column was 0.24 kg of crude methanol/water mixture and 0.31 kg of air per hour per cm² of column cross-section. The air fed in was passed through the packed column (2), where it stripped some of the methanol and water, and the resulting vapor/air mixture was then passed through two layers of wire filter (29). The layers used each comprised a packing of wire mesh consisting of stainless chromium nickel steel. In each layer, the wire diameter was 0.15 mm, and the free layer volume was 99 vol. %, based on the total volume of the layer. The flow rate of the gas/vapor mixture was 12.8 m/sec in the first layer, and 1.2 m/sec in the second layer. On passage of the gas/vapor mixture through the two layers (29), a part of it (6 kg/hour) was separated off and recycled to the packed column (2) via line (16).

The plant used contained a vertical tube reactor (12) which had at its top the feed inlet for the gaseous starting mixture and the reactor hood. The catalyst layer (27) was below the top of the reactor. Further down was a cooling zone connected to the lines (17) and (18).

A catalyst consisting of silver crystals (429 kg) and having the following composition was introduced into the reactor:

|  | Proportion of catalyst (% by weight) | Particle size mm |
|---|---|---|
| Layer 1 | 12.9 | 0.4–0.75 |
| Layer 2 | 1.2 | 0.2–0.4 |
| Layer 3 | 5.3 | 0.75–1 |
| Layer 4 | 14.1 | 1–1.75 |
| Layer 5 | 66.5 | 1–2.5 |

Layer 2 was scattered, in the form of an annular layer in the peripheral zone of the catalyst, on top of layer 3. The diameter of the catalyst was 310 cm, and the internal diameter of the annular layer was 305 cm. 42,111 kg/hour of gaseous mixture containing 28.6% by weight of methanol, 0.0026% by weight of impurities, 19.0974% by weight of water and 52.3% by weight of air were fed to the reactor from the second wire layer (29), via line 11. The mixture was passed through the catalyst, and converted at 700° C. and under 1.4 bar.

To cool the reaction gases in the reactor (12), 14,600 kg/hour of boiler feed water were fed in via line 17, and 14,600 kg/hour of excess steam (16 bar) were discharged via line (18) and used for another reaction. The reaction gases, which had been cooled to 152° C., were fed to the condenser (9) via line 20, and then to the absorption tower (22) via line (21). They were absorbed in this tower, 2,800 kg/hour of water being fed in via line (23). Absorption liquid was circu-lated through the tower (22) via line (19), exchanger (7) and line (26). The recycle liquid for the packed column was heated by the hot gases in condenser (9), which were themselves cooled to 79° C., and the absorption solutions, at 70° C., in exchanger (7). The exit gas was removed via line (28). 10,000 kg/hour (yield 88.5% of theory) of formaldehyde (calculated as 100% pure) were separated off in the form of a 40% strength by weight aqueous formaldehyde solution via line (24). The life of the catalyst was 116 days. The formaldehyde solution contained 3.8% by weight of methanol and 0.025% by weight of formic acid, the percentages being based on formaldehyde (calculated as 100% pure).

EXAMPLE 2

(Figure 1)

22,030 kg/hour of air were fed through line (1) to the packed column (2) below the surface of the bottom product of the column. Using a countercurrent procedure, 17,310 kg/hour of a crude methanol/water mixture (1% by weight of impurities, 69.6% by weight of methanol and 29.4% by weight of water) were fed via line (3) and 310,000 kg/hour of bottom product (recycle liquid) of the packed column were fed via line (4), pump (5), line (6), heat S exchanger (7), (ine (8), condenser (9) and line (10). The packed column had a length of 12.8 m and a diameter of 300 cm and contained 42 m³ of Pall rings as packing (length 3.5 cm; diameter 3.5 cm). The bottom product (recycle liquid) contained 10% by weight of impurities, 28% by weight of methanol and 62% by weight of water. In heat exchanger (7), the recycle liquid was heated to 68° C., heating being carried out indirectly with absorption liquid via line 19 by a countercurrent procedure. In condenser (9), the recycle liquid was heated indirectly by heat exchange with hot reaction gases (via line (20)) to 79° C. The temperature at the point of entry of the recycle liquid into the column (2) was 78° C., and the bottom temperature of the column (2) was 62° C. 1,730 kg/hour of recycle liquid were taken off via line (13) and were vaporized in evaporator (14), together with 3,343 kg/hour of water. 572 kg/hour of bottom product from the evaporator (172 kg of impurities and 400 kg of water) were taken off via the bottom outlet (15). The amount vaporized per hour (485 kg of methanol, 4,015.99 kg of water and 0.01 kg of impurities) was fed from evaporator (14) via line (25) to line (11). The throughput through the packed column was 0.24 kg of crude methanol/water mixture and 0.31 kg of air per hour per cm² of column cross-section. The air fed in was passed through the packed column (2), where it stripped some of the methanol and water, and the resulting vapor/air mixture was then passed through two layers of wire filter (29). The layers used each comprised a packing of wire mesh consisting of stainless chromium nickel steel. In each layer, the wire diameter was 0.28 mm, and the free layer volume was 99 vol. %, based on the total volume of the layer. The flow rate of the gas/vapor mixture was 7 m/sec in the first layer, and 3.9 m/sec in the second layer. On passage of the gas/vapor mixture through the two layers, a part of it (6 kg/hour) was separated off and recycled to the packed column (2) via line (16).

The plant used contained a vertical tube reactor (12) which had at its top the feed inlet for the vapor-phase starting mixture and the reactor hood. The catalyst layer (27) was below the top of the reactor. Further down was a cooling zone connected to the lines (17) and (18).

A catalyst consisting of silver crystals (429 kg) and having the following composition was introduced into the reactor:

| | Proportion of catalyst (% by weight) | Particle size mm |
|---|---|---|
| Layer 1 | 12.9 | 0.4–0.75 |
| Layer 2 | 1.2 | 0.2–0.4 |
| Layer 3 | 5.3 | 0.75–1 |
| Layer 4 | 14.1 | 1–1.75 |
| Layer 5 | 66.5 | 1–2.5 |

Layer 2 was scattered, in the form of an annular layer in the peripheral zone of the catalyst, on top of layer 3. The diameter of the catalyst bed was 310 cm, and the internal diameter of the annular layer was 305 cm. 42,111 kg/hour of gaseous mixture containing 28.6% by weight of methanol, 0.0026% by weight of impurities, 19.0974% by weight of water and 52.3% by weight of air were fed to the reactor from the second wire layer (29), via line 11. The mixture was passed through the catalyst, and converted at 700° C. and under 1.4 bar.

To cool the reaction gases in the reactor (12), 14,600 kg/hour of boiler feed water were fed in via line 17, and 14,600 kg/hour of excess steam (16 bar) were discharged via line (18) and used for another reaction. The reaction gases, which had been cooled to 152° C., were fed to the condenser (9) via line 20, and then to the absorption tower (22) via line (21). They were absorbed in this tower, 2,800 kg/hour of water being fed in via line (23). Absorption liquid was circulated through the tower (22) via line (19), exchanger (7) and line (26). The recycle liquid of the packed column was heated by the hot gases in condenser (9), which were themselves cooled to 79° C., and the absorption solutions, at 70° C., in exchanger (7). The exit gas was removed via line (28). 10,000 kg/hour (yield 88.5% of theory) of formaldehyde (calculated as 100% pure) were separated off in the form of a 40% strength by weight aqueous formaldehyde solution via line (24). The life of the catalyst was 116 days. The formaldehyde solution contained 3.2% by weight of methanol and 0.022% by weight of formic acid, the percentages being based on formaldehyde (calculated as 100% pure).

EXAMPLE 3

Figure 2:
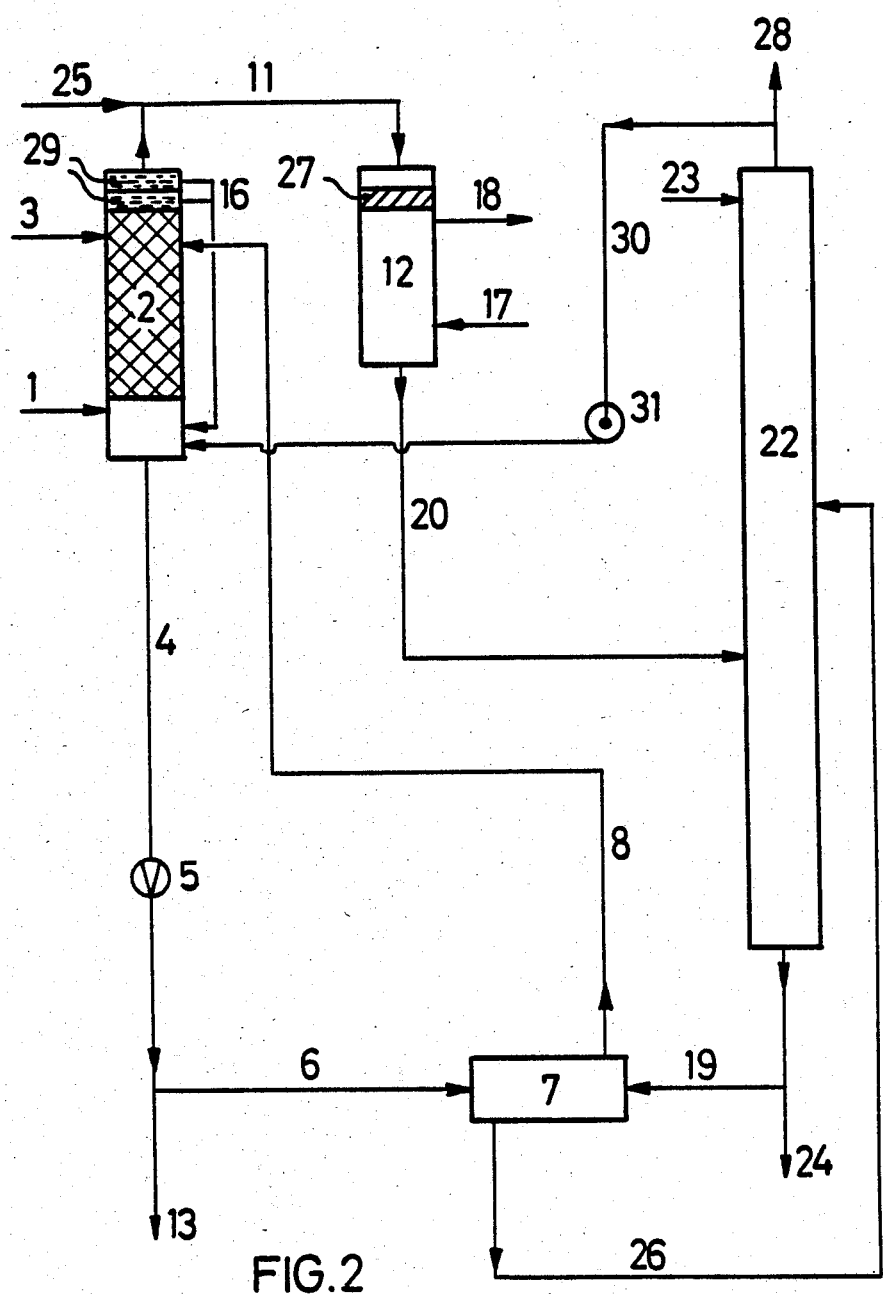

(Figure 2)

5,885 kg/hour of air were fed into the packed column (2) through line (1) and 3,290 kg/hour of exit gas (1.3% by weight of $H_2$, 0.5% by weight of CO and 6.9% by weight of $CO_2$) were fed into the said column through line (30) and pump (31), the feeds being introduced below the surface of the bottom product of the column. Using a countercurrent procedure, 4050 kg/hour of a crude methanol/water mixture (0.3% by weight of impurities, 75.8% by weight of methanol and 23.9% by weight of water) were fed via line (3) and 117,000 kg/hour of bottom product (recycle liquid) of the packed column were fed via line (4), pump (5), line (6), heat exchanger (7) and line (8). The packed column had a length of 9 m and a diameter of 180 cm and contained 12.5 m³ of Pall rings as packing (length 3.5 cm, diameter 3.5 cm). The bottom product (recycle liquid) contained 10% by weight of impurities, 33.3% by weight of methanol and 56.7% by weight of water. In the heat exchanger (7), the recycle liquid was heated indirectly to 59° C. with absorption liquid via line 19 by a countercurrent procedure. The temperature at the point of entry of the recycle liquid into the column (2) was 59° C., and the temperature at the bottom of the column (2) was 49° C. 120 kg/hour of recycle liquid (40 kg of methanol, 68 kg of water and 12 kg of impurities) were taken off via line (13). The throughput through the packed column was 0.16 kg of freshly fed in crude methanol/water mixture, 0.23 kg of air and 0.13 kg of exit gas per hour per cm² of column cross-section. The air and exit gas fed in were passed through the packed column (2), where they stripped some of the methanol and water, and the resulting vapor-gas mixture was then passed through two layers of wire filter (29). Each of the layers used comprised a packing of wire mesh consisting of stainless chromium nickel steel. In each layer, the wire diameter was 0.4 mm and the free layer volume was 95 vol. %, based on the total volume of the layer. The flow rate of the gas/vapor mixture was 13 m/sec in the first layer and 4 m/sec in the second layer. On passage of the gas-vapor mixture through the two layers (29), some of it (2 kg/hour) was separated off and recycled to the packed column (2) via line (16).

The plant used contained a vertical tube reactor (12) which had at its top the feed inlet for the vapor-phase starting mixture and the reactor hood. The catalyst layer (27) was below the top of the reactor. Further down was a cooling zone connected to the lines (17) and (18).

A catalyst consisting of silver crystals (187 kg) and having the following composition was introduced into the reactor:

| | Proportion of catalyst (% by weight) | Particle size mm |
|---|---|---|
| Layer 1 | 12.9 | 0.4–0.75 |
| Layer 2 | 1.2 | 0.2–0.4 |
| Layer 3 | 5.3 | 0.75–1 |
| Layer 4 | 14.1 | 1–1.75 |

|  | Proportion of catalyst (% by weight) | Particle size mm |
| --- | --- | --- |
| Layer 5 | 66.5 | 1–2.5 |

Layer 2 was scattered, in the form of an annular layer in the peripheral zone of the catalyst, on top of layer 3. The diameter of the catalyst bed was 170 cm, and the internal diameter of the annular layer was 160 cm. 13,104 kg/hour of gaseous mixture which, in addition to exit gas, contained 23% by weight of methanol, 0.0014% by weight of impurities, 8.8% by weight of water and 44.9% by weight of air were fed to the reactor from the second wire layer (29), via line (11). The mixture was passed through the catalyst, and converted at 700° C. and under 1.3 bar.

To cool the reaction gases in the reactor (12), 4,710 kg/hour of boiler feed water were fed in via line (17), and 4,710 kg/hour of excess steam (5 bar) were discharged via line (18) and used for another reaction. The reaction gases, which had been cooled to 180° C., were fed into the absorption tower (22) via line (20). They were absorbed in this tower, 199 kg/hour of water being fed in via line (23). Absorption liquid was circulated through the tower (22) via line (19), exchanger (7) and line (26). The recycle liquid for the packed column was heated by the absorption solutions, at 76° C., in exchanger (7). The exit gas was removed via line (28). 2,546 kg/hour (yield 88.5% of theory) of formaldehyde (calculated as 100% pure) were separated off in the form of a 50% strength by weight aqueous formaldehyde solution via line (24). The life of the catalyst was 116 days. The formaldehyde solution contained 2.4% by weight of methanol and 0.02% by weight of formic acid, the percentages being based on formaldehyde (calculated as 100% pure).

EXAMPLE 4

(Figure 2)

5,885 kg/hour of air were fed into the packed column (2) through line (1) and 3,290 kg/hour of exit gas (composition similar to that of Example 3) were fed into the said column through line (30) and pump (31), the feeds being introduced below the surface of the bottom product of the column. Using a countercurrent procedure, 4050 kg/hour of a crude methanol/water mixture (0.3% by weight of impurities, 75.8% by weight of methanol and 23.9% by weight of water) were fed via line (3) and 117,000 kg/hour of bottom product (recycle liquid) of the packed column were fed via line (4), pump (5), line (6), heat exchanger (7) and line (8). The packed column had a length of 9 m and a diameter of 180 cm and contained 2,500 l of Pall rings having a length of 5 cm and a diameter of 5 cm as packing in the lower region and, as packing above this, 10,000 l of Pall rings having a length of 3.5 cm and a diameter of 3.5 cm. The bottom product (recycle liquid) contained 10% by weight of impurities, 33.3% by weight of methanol and 56.7% by weight of water. In the heat exchanger (7), the recycle liquid was heated indirectly to 59° C. with absorption liquid via line 19 by a countercurrent procedure. The temperature at the point of entry of the recycle liquid into the column (2) was 59° C., and the temperature at the bottom of the column (2) was 49° C. 120 kg/hour of recycle liquid (40 kg of methanol, 68 kg of water and 12 kg of impurities) were taken off via line (13). The throughput through the packed column was 0.16 kg of freshly fed in crude methanol/water mixture, 0.23 kg of air and 0.13 kg of exit gas per hour per $cm^2$ of column cross-section. The air fed in was passed through the packed column (2), where it stripped some of the methanol and water, and the resulting vapor-air mixture was then passed through two layers of wire filter (29). Each of the layers used comprised a packing of wire mesh consisting of stainless chromium nickel steel. In each layer, the wire diameter was 0.3 mm and the free layer volume was 95 vol. %, based on the total volume of the layer. The flow rate of the gas/vapor mixture was 7 m/sec in the first layer and 1 m/sec in the second layer. On passage of the gas-vapor mixture through the two layers (29), some of it (2 kg/hour) was separated off and recycled to the packed column (2) via line (16).

The plant used contained a vertical tube reactor (12) which had at its top the feed inlet for the vapor-phase starting mixture and the reactor hood. The catalyst layer (27) was below the top of the reactor. Further down was a cooling zone connected to the lines (17) and (18).

A catalyst consisting of silver crystals (187 kg) and having the following composition was introduced into the reactor:

|  | Proportion of catalyst (% by weight) | Particle size mm |
| --- | --- | --- |
| Layer 1 | 12.9 | 0.4–0.75 |
| Layer 2 | 1.2 | 0.2–0.4 |
| Layer 3 | 5.3 | 0.75–1 |
| Layer 4 | 14.1 | 1–1.75 |
| Layer 5 | 66.5 | 1–2.5 |

Layer 2 was scattered, in the form of an annular layer in the peripheral zone of the catalyst, on top of layer 3. The diameter of the catalyst bed was 190 cm, and the internal diameter of the annular layer was 180 cm. 13,104 kg/hour of gaseous mixture which, in addition to exit gas, contained 23% by weight of methanol, 0.00009% by weight of impurities, 8.8% by weight of water and 44.9% by weight of air were fed to the reactor from the second wire layer (29), via line 11. The mixture was passed through the catalyst, and converted at 700° C. and under 1.3 bar.

To cool the reaction gases in the reactor (12), 4,710 kg/hour of boiler feed water were fed in via line (17), and 4,710 kg/hour of excess steam (5 bar) were discharged via line (18) and used for another reaction. The reaction gases, which had been cooled to 180° C., were fed into the absorption tower (22) via line (20). They were absorbed in this tower, 199 kg/hour of water being fed in via line (23). Absorption liquid was circulated through the tower (22) via line (19), exchanger (7) and line (26). The recycle liquid for the packed column was heated by the absorption solutions, at 76° C., in line (19). The exit gas was removed via line (28). 2,546 kg/hour (yield 88.5% of theory) of formaldehyde (calculated as 100% pure) were separated off in the form of a 50% strength by weight aqueous formaldehyde solution via line (24). The life of the catalyst was 120 days. The formaldehyde solution contained 2.4% by weight of methanol and 0.02% by weight of formic acid, the percentages being based on formaldehyde (calculated as 100% pure).

EXAMPLE 5 (Comparison)

(Figure 1)

22,030 kg/hour of air were fed through line (1) to the packed column (2) below the surface of the bottom product of the column. Using a countercurrent procedure, 17,310 kg/hour of a crude methanol/water mixture (1% by weight of impurities, 69.6% by weight of methanol and 29.4% by weight of water) were fed via line (3) and 310,000 kg/hour of bottom product (recycle liquid) of the packed column were fed via line (4), pump (5), line (6), heat exchanger (7), line (8), condenser (9) and line (10). The packed column had a length of 12.8 m and a diameter of 300 cm and contained 42 m³ of Pall rings as packing (length 3.5 cm; diameter 3.5 cm). The bottom product (recycle liquid) contained 4.7% by weight of impurities, 28% by weight of methanol and 67.3% by weight of water. In heat exchanger (7), the recycle liquid was heated to 68° C., heating being carried out indirectly with absorption liquid via line 19 by a countercurrent procedure. In condenser (9), the recycle liquid was heated indirectly by heat exchange with hot reaction gases (via line (20)) to 79° C. The temperature at the point of entry of the recycle liquid into the column (2) was 78° C., and the bottom temperature of the column (2) was 62° C. 1,730 kg/hour of recycle liquid were taken off via line (13) and were vaporized in evaporator (14), together with 3,343 kg/hour of water. 480 kg/hour of bottom product from the evaporator (80 kg of impurities and 400 kg of water) were taken off via the bottom outlet (15). The amount vaporized per hour (484.5 kg of methanol, 4,108 kg of water and 0.5 kg of impurities) was fed from evaporator (14) via line (25) to line (11). The throughput through the packed column was 0.24 kg of crude methanol/water mixture and 0.31 kg of air per hour per cm² of column cross-section. The air fed in was passed through the packed column (2), where it stripped some of the methanol and water, and the resulting vapor/air mixture was then passed through one layer of wire filter (29). The layer used comprised a packing of wire mesh consisting of stainless chromium nickel steel. In the layer, the wire diameter was 0.55 mm, and the free layer volume was 88 vol. %, based on the total volume of the layer. The flow rate of the gas/vapor mixture was 0.9 m/sec in the layer. On passage of the gas/vapor mixture through the layer (29), a part of it (6 kg/hour) was separated off and recycled to the packed column (2) via line (16).

The plant used contained a vertical tube reactor (12) which had at its top the feed inlet for the vapor-phase starting mixture and the reactor hood. The catalyst layer (27) was below the top of the reactor. Further down was a cooling zone connected to the lines (17) and (18).

A catalyst consisting of silver crystals (429 kg) and having the following composition was introduced into the reactor:

|  | Proportion of catalyst (% by weight) | Particle size mm |
| --- | --- | --- |
| Layer 1 | 12.9 | 0.4–0.75 |
| Layer 2 | 1.2 | 0.2–0.4 |
| Layer 3 | 5.3 | 0.75–1 |
| Layer 4 | 14.1 | 1–1.75 |
| Layer 5 | 66.5 | 1–2.5 |

Layer 2 was scattered, in the form of an annular layer in the peripheral zone of the catalyst, on top of layer 3. The diameter of the catalyst bed was 310 cm, and the internal diameter of the annular layer was 305 cm. 42,203 kg/hour of gaseous mixture containing 28.55% by weight of methanol, 0.22% by weight of impurities, 19.03% by weight of water and 52.2% by weight of air were fed to the reactor from the wire layer (29), via line 11. The mixture was passed through the catalyst, and converted at 700° C. and under 1.4 bar.

To cool the reaction gases in the reactor (12), 14,600 kg/hour of boiler feed water were fed in via line 17, and 14,600 kg/hour of excess steam (16 bar) were discharged via line (18) and used for another reaction. The reaction gases, which had been cooled to 152° C., were fed to the condenser (9) via line 20, and then to the absorption tower (22) via line (21). They were absorbed in this tower, 2,800 kg/hour of water being fed in via line (23). Absorption liquid was circulated through the tower (22) via line (19), exchanger (7) and line (26). The recycle liquid of the packed column was heated by the hot gases in condenser (9), which were themselves cooled to 79° C., and the absorption solutions, at 70° C., in exchanger (7). The exit gas was removed via line (28). 9,819 kg/hour (yield 86.9% of theory) of formaldehyde (calculated as 100% pure) were separated off in the form of a 40% strength by weight aqueous formaldehyde solution via line (24). The life of the catalyst was 20 days. The formaldehyde solution contained 5.8% by weight of methanol and 0.1% by weight of formic acid, the percentages being based on formaldehyde (calculated as 100% pure).

EXAMPLE 6

(Figure 1)

The plant used was the same as that described in Example 1. No recycle liquid was taken off via line (13), and 3,343 kg of water were additionally fed in via line (25). The reaction was carried out similarly to Example 1, using methanol instead of crude methanol and without stage e (no passage through the wire layers.) 10,000 kg/hour (yield 88.5% of theory) of formaldehyde (calculated as 100% pure ) were obtained in the form of a 40% strength by weight formaldehyde solution. The life of the catalyst was 120 days. The formaldehyde solution contained 3.2% by weight of methanol and 0.025% by weight of formic acid, the percentages being based on formaldehyde (calculated as 100% pure).

We claim:

1. A process for the preparation of formaldehyde by oxidative dehydrogenation of methanol as a mixture with water, in the presence of a silver catalyst at elevated temperatures, and subsequent cooling and absorption of the hot reaction gases, wherein (a) a mixture of methanol and water with a concentration of from 50 to 90% by weight, based on the total weight of the two substances, of methanol is passed into a packed column which possesses a packing, having a total layer thickness of not less than 50 cm and a total surface area of not less than 0.5 cm² per cm³ of packing, a liquid circulation of from 15 to 90 g/min per g/min of methanol fed to the column, and a concentration of from 10 to 45% by weight of methanol in the recycle liquid, the temperature at the point of entry of the recycle liquid into the column being from 50 to 86° C. and the bottom temperature being 10°–25° C. lower than this entry temperature, i.e. from 40° to 70° C., (b) methanol and water are separated off from the packed column with air, an inert gas and/or exit gas by stripping, the throughput being from 0.5 to 3 tonnes of methanol and water per hour per m² of column cross-section, (c) the resulting gaseous mixture of methanol, water, air, inert gas and/or exit gas is converted, at a space velocity of from 0.5 to 3 tonnes of methanol per m² of catalyst bed cross-section per hour, in the presence of a silver catalyst and at from 550° to 750° C., and (d) finally, the hot reaction gases are cooled and absorbed, the resulting heat of absorption, the heat of reaction and/or the heat of condensation being partly or completely used for heating the recycle liquid.

2. A process as claimed in claim 1, wherein methanol containing impurities is used, and the measures of stages (a) and (b), then the measures of a stage (e), wherein the resulting gaseous mixture of methanol, water, air, inert gas and/or exit gas is passed through two layers of wire filter having a wire diameter of from 0.1 to 0.5 mm and a free layer volume of from 90 to 99.5 vol. %, based on the total volume of one wire layer, at a flow rate of from 7 to 13 m/sec in the first layer and from 1 to 4 m/sec in tne second layer, and finally, using the gaseous mixture, the measures of the stages (c) and (d) are carried out.

3. A process as claimed in claim 1, wherein the reaction is carried out with a methanol/water mixture being fed in which has a concentration of from 60 to 85% by weight of methanol in the aqueous mixture.

4. A process as claimed in claim 1, wherein the reaction is carried out with the water being fed in separately in an amount between 0.11 and 1 g per g of methanol.

5. A process as claimed in claim 1, wherein the reaction is carried out using crude methanol containing from 0.15 to 6% by weight of impurities.

6. A process as claimed in claim 1, wherein the reaction is carried out using a ratio of from 0.25 to 0.6 mole of oxygen, in the form of air, per mole of methanol, and from 0.1 to 2 moles of oxygen, in the form of air, per mole of total water present in the starting mixture.

7. A process as claimed in claim 1, wherein the reaction is carried out with throughputs through the packed column of from 0.5 to 3 tonnes of freshly fed in water and methanol and from 1.2 to 4.5 tonnes of air or from 0.4 to 2.5 tonnes of inert gas or from 0.4 to 2.5 tonnes of exit gas or from 1.6 to 7.0 tonnes of a mixture of two components or of all three of the components air, inert gas and exit gas, the throughputs being per hour per m² of column cross-section.

8. A process as claimed in claim 1, wherein the reaction is carried out using from 20 to 100% by weight of inert gas and/or from 20 to 100% by weight of exit gas, the percentages being based on the total weight of air.

9. A process as claimed in claim 1, wherein the reaction is carried out with a total surface area of the packing of from 0.5 to 2.2 cm² per cm³ of packing.

10. A process as claimed in claim 1, wherein the reaction is carried out using a total thickness (height) of the packing layer of from 100 to 1,000 cm.

11. A process as claimed in claim 1, wherein the reaction is carried out using a throughput of the recycle liquid of from 3,000 to 6,000 g per cm² of column cross-section per hour.

12. A process as claimed in claim 1, wherein the reaction is carried out using a recycle liquid in the form of an aqueous methanol mixture containing from 15 to 40% by weight of methanol, and a ratio of from 20 to 70 g/minute per g/minute of fresh methanol fed to the column.

13. A process as claimed in claim 1, wherein the reaction is carried out with a temperature at the entry point into the column of from 60° to 80° C. and a temperature at the bottom of the column of from 45° to 60° C.

14. A process as claimed in claim 1, wherein the reaction is carried out using a space velocity, during the oxidation, of from 0.5 to 3 g (calculated as 100% pure) of methanol per m² of catalyst bed cross-section per hour, at from 550° to 750° C. and under a pressure between 0.5 and 2 bar, by a continuous procedure.

15. A process as claimed in claim 2, wherein the stage e is carried out using wire in the two layers, the diameter (wire thickness) being from 0.1 to 0.3 mm and the free layer volume being from 95 to 99.1 vol. %, based on the total volume of the layer.

16. A process as claimed in claim 2, wherein the stage e is carried out, in the first layer, using a velocity of from 9 to 11 m/sec and a throughput of from 12 to 60 g of methanol per minute per cm² of layer cross-section.

17. A process as claimed in claim 2, wherein the stage 3 is carried out, in the second layer, using a velocity of from 1.5 to 3.5 m/sec and a throughput of from 1 to 20 g of methanol per minute per cm² of layer cross-section.

18. A process as claimed in claim 2, wherein the stage e is carried out using a layer thickness of from 10 to 40 cm for each of the two layers.

* * * * *